United States Patent [19]

Kurono et al.

[11] 4,124,765
[45] Nov. 7, 1978

[54] 5-FLUOROURACIL DERIVATIVES

[75] Inventors: Masayasu Kurono, Osaka; Takeshi Chiba, Takatsuki; Setsuro Fujii, Tokushima, all of Japan

[73] Assignee: Ono Pharmaceutical Co., Ltd., Osaka, Japan

[21] Appl. No.: 727,422

[22] Filed: Sep. 28, 1976

Related U.S. Application Data

[63] Continuation-in-part of Ser. No. 577,085, May 13, 1975, abandoned.

[51] Int. Cl.² .......................................... C07D 239/54
[52] U.S. Cl. .................................................... 544/313
[58] Field of Search ........................................ 260/260

[56] References Cited

U.S. PATENT DOCUMENTS

| | | | |
|---|---|---|---|
| 3,322,526 | 5/1967 | Loux | 260/260 |
| 3,682,917 | 8/1972 | Knuniants et al. | 260/260 |
| 3,912,734 | 10/1975 | Giller et al. | 260/260 |
| 3,971,784 | 7/1976 | Tada | 260/260 |

FOREIGN PATENT DOCUMENTS

| | | | |
|---|---|---|---|
| 50-37,787 | 4/1975 | Japan | 260/260 |
| 51-19,778 | 2/1976 | Japan. | |

*Primary Examiner*—Paul M. Coughlan, Jr.
*Attorney, Agent, or Firm*—Armstrong, Nikaido, Marmelstein & Kubovcik

[57] ABSTRACT

5-Fluorouracil derivatives and a process for their preparation are provided. The 5-fluorouracil derivatives according to the invention have the general formula:

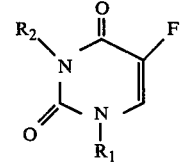

$R_1$ and $R_2$ are the same or different and are hydrogen or

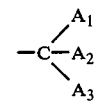

with the proviso that both $R_1$ and $R_2$ are not hydrogen at the same time. $A_1$, $A_2$ and $A_3$ are independently selected from hydrogen, and optionally substituted alkoxy and phenyloxy; at least one of $A_1$, $A_2$ and $A_3$ being other than hydrogen. The 5-fluorouracil derivative is prepared by condensing 5-fluorouracil with a halide of the formula:

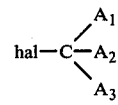

in the presence of a base. The 5-fluorouracils according to the invention show anti-tumor activity.

8 Claims, No Drawings

5-FLUOROURACIL DERIVATIVES

This is a continuation-in-part application of application Ser. No. 577,085, filed May 13, 1975, now abandoned.

BACKGROUND OF THE INVENTION

1. Field of the Invention

This invention relates to novel 5-fluorouracil derivatives and the preparation thereof.

2. Description of the Prior Art

Substituted uracils are known in the art. These include 5-fluorouracil; $N^1$-(2'-furanidyl)-5-fluorouracil (FT-207); substituted hydrouracil derivatives and 6-alkyluracil derivatives and are disclosed in U.S. Pat. No. 2,802,005; R. Duschinsky et al, J. Am. Chem. Soc., 79, 4559 (1957); I. L. Knuniants et al, U.S. Pat. No. 3,682,917; I. Feldman et al, Med. Prom. SSSR., 19, 3, 12 (1965); S. A. Giller et al, British Pat. No. 1,168,391; S. A. Giller et al, U.S. Pat. No. 3,912,734; H. M. Loux et al, U.S. Pat. No. 3,322,526; and H. M. Loux et al, Belgian Pat. No. 625,897.

It is an object of the present invention to provide a new class of uracil derivatives, more particularly, 5-fluorouracil derivatives. This and other objects will be apparent from the following summary and description of preferred embodiments.

SUMMARY OF THE INVENTION

According to the present invention there are provided fluorouracil derivatives represented by the general formula (I):

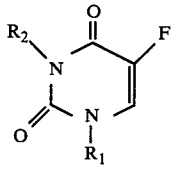

wherein $R_1$ and $R_2$ are the same or different and are hydrogen or

with the proviso that both $R_1$ and $R_2$ are not hydrogen at the same time; and wherein $A_1$, $A_2$ and $A_3$ are independently selected from hydrogen; alkoxy ($R_3O-$, where $R_3$ is straight or branched chain alkyl of from 1 to 10 carbon atoms or cycloalkyl of from 4 to 6 carbon atoms) and phenyloxy ($R_4O-$, where $R_4$ is a phenyl group); the alkoxy and phenyloxy being unsubstituted or substituted with fluoro, chloro, bromo, iodo, hydroxy, phenyloxy, acetoxy, alkoxy of 1 to 5 carbon atoms, or alkyl or alkenyl of 1 to 5 carbon atoms and which may be substituted with fluoro, chloro, bromo, iodo, methoxy or hydroxy; at least one of $A_1$, $A_2$ and $A_3$ being other than hydrogen.

The 5-fluorouracil derivatives (I) are prepared by condensing 5-fluorouracil with a halide of the formula (II):

$$\text{hal}-\text{C}\begin{smallmatrix}\nearrow A_1 \\ -A_2 \\ \searrow A_3\end{smallmatrix} \quad \text{(II)}$$

where hal represents a halogen atom and $A_1$, $A_2$ and $A_3$ are as defined above.

DESCRIPTION OF PREFERRED EMBODIMENTS

The members $A_1$, $A_2$ and $A_3$ of the halide (II) are selected from among hydrogen, alkoxy and phenyloxy, at least one of $A_1$, $A_2$ and $A_3$ being other than hydrogen. The alkoxy and phenyloxy groups may be unsubstituted or substituted with fluorine, chlorine, bromine, iodine, hydroxy, phenyloxy, acetoxy, alkoxy of 1 to 5 carbon atoms or alkyl or alkenyl of 1 to 5 carbon atoms. The alkyl and alkenyl substituents may, in turn, be substituted with fluorine, chlorine, bromine, iodine, methoxy or hydroxy. Substitution of the alkoxy and phenyloxy groups will typically be limited to a single substituent although the only limitation with respect to such substitution is believed to be the availability, or existence, of the compounds (II). In other words, all available compounds within the definition of the compound (II) are believed to be operable in the environment of the presently claimed invention. Similar considerations apply to the substitution of the alkyl and alkenyl groups. Examples of the substitution of the alkoxy, phenyloxy, alkyl and alkenyl groups may be seen from the following detailed description, table and working examples.

The reaction between the 5-fluorouracil and the halide (II) is carried out in an inert solvent. The solvent is preferably selected from aprotic solvents such as, for example, N,N-dimethylformamide, N,N-dimethylacetamide, tetramethylurea, dimethylsulfoxide, hexamethylphosphoramide and the like.

The reaction is conducted in the presence of a base. The base may be selected from alkali metal carbonates and alkali metal hydrogen carbonates. However, from the standpoints of availability and handling easiness, it is preferable to use potassium carbonate.

Each of the base and the halide (II) is used in an amount of one equivalent or more relative to the amount of the 5-fluorouracil. When one equivalent of each of the base and the halide of the formula (II) is used relative to the 5-fluorouracil, the product will comprise $N^1$-mono-substituted-5-fluorouracil, $N^3$-mono-substituted-5-fluorouracil and $N^1,N^3$-disubstituted-5-fluorouracil. However, when excess amounts, for example, more than two equivalents, of the base and the halide are used, the product will comprise $N^1,N^3$-disubstituted-5-fluorouracil only.

The reaction temperature may vary a wide range. Preferably, however, the reaction is conducted at a temperature ranging from about normal, or ambient, temperature (about 20° C.) to about 80° C. The reaction time will vary with the reaction temperature, but generally is in the range of 1–12 hours.

The condensation reaction may easily be detected and monitored since carbon dioxide will be generated simultaneously with the starting of the reaction. The end point of the reaction is also detectable by the ceasing of the generation of carbon dioxide.

In order for the reaction to proceed smoothly it is preferable to add a small amount of sodium iodide as a catalyst.

When the reaction is completed by the cessation of the generation of carbon dioxide, water is added to the reaction mixture in approximately the same amount as the amount of reaction solvent used, the mixture is acidified with a dilute mineral acid, preferably to a pH of about 2.0, and the product is extracted several times with chloroform. The chloroform extract obtained is dried over a drying agent as, for example, magnesium sulfate, and concentrated by stripping the chloroform off to obtain a crude product. In purifying the crude product, column chromatography is used employing about 5–20 times, by weight, of silica gel. As an eluent, a mixture of benzene and ethylacetate (1:1 by volume) is used. By this elution, pure an $N^1,N^3$-disubstitution product, $N^1$-mono-substitution product and $N^3$-mono-substitution product are obtained in order.

The halide of the formula (II) which may be employed according to the present invention includes, for example, methoxychloromethane; ethoxychloromethane; propoxychloromethane; butoxybromomethane; heptoxybromomethane; decoxychloromethane; cyclobutoxychloromethane; cyclopentoxychloromethane; cyclohexoxychloromethane; 2,2-di-fluorocyclobutoxychloromethane; 4-chlorocyclohexoxychloromethane; isopropyloxychloromethane; isobutoxychloromethane; sec-butoxychloromethane; neopentoxychloromethane; allyloxychloromethane; 2-butenyloxychloromethane; 2,2,2-trichloroethoxychloromethane; 2-chloroethoxychloromethane; 2-fluoroethoxychloromethane; 2,2,2-trifluoroethoxychloromethane; 3-bromopropoxychloromethane; 7-iodoheptoxychloromethane; 2-acetoxyethoxychloromethane; 2-methoxyethoxychloromethane; 2-ethoxyethoxychloromethane; 2-phenyloxyethoxychloromethane; 2-p-chlorophenyloxyethoxychloromethane; phenyloxychloromethane; p-chlorophenyloxychloromethane; p-methoxyphenyloxychloromethane; and m-methylphenyloxychloromethane.

The halide of the formula (II) may be prepared according to known methods. For example, equivalent quantities of a corresponding alcohol and trioxymethylene were treated with dry hydrogen chloride in a reaction flask surrounded with an ice-bath in order to remove the heat generated during reaction and at the same time to increase the solubility of the hydrogen chloride. After a state of saturation had been reached the product was separated from the aqueous hydrochloric layer and dried over fused calcium chloride (see J. W. Farren et al, J. Am. Chem. Soc., 47, 2419, (1925)).

The 5-fluorouracil derivatives of the general formula (I) of this invention have anti-tumor activities on Sarcoma-180, as shown in Table I.

TABLE I

EFFECTS OF 5-FLUOROURACIL AND 5-FLUOROURACIL DERIVATIVES ON SARCOMA - 180 (SOLID TYPE)

| Agent | Administration | Dose 100mg/kg T/C.B.W.** | Dose 100mg/kg T/C.T.W.* | Dose 200mg/kg T/C.B.W.** | Dose 200mg/kg T/C.T.W.* |
|---|---|---|---|---|---|
| $N^1$—$CH_2OCH_3$ | po. | | | 0.83 | 0.504 |
| $N^1$—$CH_2OCH_2CH_3$ | po. | 1.02 | 0.625 | 0.85 | 0.088 |
| $N^1$—$CH_2OCH_2CH_2CH_3$ | po. | | | 1.04 | 0.417 |
| $N^1$—$CH_2OCH_2CH_2CH_2CH_3$ | po. | | | 0.78 | 1.695 |
| $N^1$—$CH_2OCH_2(CH_2)_5CH_3$ | ip. | | | 0.80 | 0.514 |
| $N^1,N^3$—$(CH_2OCH_3)_2$ | ip. | | | 0.87 | 0.864 |
| $N^3$—$CH_2OCH_2CH_3$ | po. | | | 0.71 | 0.345 |
| $N^1$—$CH_2OCH_2CH$=$CH_2$ | po. | | | 0.36 | 1.276 |
| $N^1$—$CH_2OCH(CH_3)CH_3$ | po. | 0.83 | 0.458 | 0.46 | 0.065 |
| 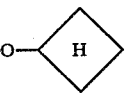 | po. | | | 1.17 | 1.060 |
| 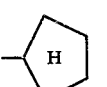 | po. | | | 0.76 | 0.135 |
| 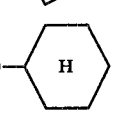 | po. | | | 0.78 | 1.157 |
| $N^1$—$CH_2OCH_2Cl_3$ | po. | | | 0.85 | 0.824 |
| $N^1$—$CH_2OCH_2CH_2Cl$ | po. | | | 0.68 | 0.155 |
| $N^1$—$CH_2OCH_2CF_3$ | po. | | | 0.42 | 0.866 |
| $N^1$—$CH_2OCH_2CH_2F$ | po. | 0.58 | (10mg/kg) 0.741 | | |
| $N^1$—$CH_2OCH_2CH_2OCOCH_3$ | po. | | | 1.17 | 1.011 |
| $N^1$—$CH_2OCH_2CH_2OH$ | po. | | | 0.50 | 1.041 |
| $N^1$—$CH_2OCH_2CH_2OCH_3$ | po. | | | 0.60 | 1.173 |
| $N^1$—$CH_2OCH_2CH_2OCH_2CH_3$ | po. | | | 0.46 | 1.276 |
| 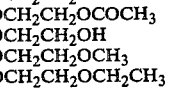 | po. | | | 0.98 | 0.652 |
| 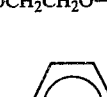 | po. | | | 0.60 | 1.242 |

TABLE I-continued
EFFECTS OF 5-FLUOROURACIL AND 5-FLUOROURACIL DERIVATIVES ON SARCOMA - 180 (SOLID TYPE)

| Agent | Administration | Dose 100mg/kg | | Dose 200mg/kg | |
|---|---|---|---|---|---|
| | | T/C.B.W.** | T/C.T.W.* | T/C.B.W.** | T/C.T.W.* |
| $N^1$—$CH_2O$—〈ring〉—$OCH_3$ | po. | | | 0.09 | 1.094 |
| $N^1$—$CH_2O$—〈ring〉—Cl | po. | | | 0.23 | 0.655 |
| $N^1,N^3$—$(CH_2O$—〈ring〉—$Cl)_2$ | ip. | | | 0.94 | 1.090 |
| FT-207 | po. | 1.01 | 0.539 | 0.39 | 0.147 |
| FT-207 | ip. | 0.60 | 0.269 | | |
| 5-fluorouracil | po. | 0.73 | (30mg/kg) 0.387 | 0.15 | (44mg/kg) 0.126 |

*The ratio of the treated to control average tumor weight.
**The ratio of the treated to control average body weight change from onset to 9th day.

The data of Table I were obtained by transplanting Sarcoma-180 subcutaneously into the left groin of mice. From the day following the day of tumor implantation, the anti-tumor agents were administered orally or intraperitoneally for 7 days. On the 9th day after tumor implantation, the mice were killed and tumors were extirpated and weighed.

The data suggest that clinical use of the 5-fluorouracil derivatives of the general formula (I), for example, $N^1$-ethoxymethyl-5-fluorouracil; $N^1$-isopropoxymethyl-5-fluorouracil and $N^1$-cyclopentoxymethyl-5-fluorouracil are advantageous for their anti-tumor activity and safety.

For a better understanding of the invention, the following examples of practical embodiments thereof are given by way of illustration.

EXAMPLE I

To a suspension of 5-fluorouracil (5.00 g, 38.4 m. mol), potassium carbonate (5.30 g, 38.4 m. mol) and sodium iodide (1.80 g, 12.8 m. mol) in dimethylsulfoxide (30 ml) was added a solution of p-chlorophenoxychloromethane (6.80 g, 38.4 m. mol) in dimethylsulfoxide (20 ml). The reaction mixture was stirred at 50° C. for 1 hour. After confirming that the reaction was finished by the cessation of the generation of carbon dioxide, the reaction mixture was diluted with water (50 ml) and acidified with 3% hydrochloric acid to pH 2.0, and the product extracted with chloroform (4 × 8 ml). The combined chloroform extracts were dried over magnesium sulfate and concentrated by stripping the chloroform off to yield a crude product. The mixed products were separated and purified by column chromatography on silica gel using as an eluting solvent a mixture of benzene and ethyl acetate (1:1) to give three products having the following physical characteristics and in the following order:

$N^1,N^3$-di-(p-chlorophenoxmethyl)-5-fluorouracil; 5.208 g (66% yield), m.p. 90° C.
NMR(CDCl$_3$): δ ppm; 5.48 (2H, singlet), 5.72 (2H, singlet), 6.7–7.5 (9H, multiplet)
IR(film): ν cm$^{-1}$; 1721, 1660
UV(Dioxane-H$_2$O; 50%): λ $_{max}^{pH=7.0}$, nm(ε); 267 (6600)

Mass spectrum: m/e = 412, 411, 410 (M$^+$), 143, 141 (C$_7$H$_6$OCl)
Analysis: Calcd. for C$_{18}$H$_{13}$FN$_2$O$_4$Cl$_2$: C=52.56; H=3.18; N=6.81; F=4.62. Found: C=50.30; H=3.10; N=6.59; F=4.48.

$N^1$-p-chlorophenoxymethyl-5-fluorouracil: 353 mg. (3.4% yield), m.p. 126°–127° C.
NMR(CDCl$_3$-DMSO-d$_6$): δ ppm; 5.49 (2H, singlet), 6.83 (2H, doublet), 7.10 (2H, doublet) 7.35 (2H, doublet)
IR(KBr): ν cm$^{-1}$; 1700
UV(Dioxane-H$_2$O; 50%): λ $_{max}^{pH=7.0}$, nm(ε); 260 (8300)
Mass spectrum: m/e = 272, 270 (M$^+$); 143 (M—C$_6$H$_4$OCl)
Analysis: Calcd. for C$_{11}$H$_8$FN$_2$O$_3$Cl: C=48.81; H=2.98; N=10.35; F=7.02. Found: C=48.67; H=2.90; N=10.18; F=6.98.

$N^3$-p-chlorophenoxymethyl-5-fluorouracil: 312 mg. (3.0% yield), solid
NMR(CDCl$_3$-DMSO-d$_6$): δ ppm; 5.60 (2H, singlet), 6.90 (2H, doublet), 7.08 (2H, doublet), 7.30 (2H, doublet)
IR(KBr): ν cm$^{-1}$; 1670, 1655
UV(Dioxane-H$_2$O; 50%): λ $_{max}^{pH=7.0}$, nm(ε); 267 (8600)
Mass spectrum: m/e = 272, 270 (M$^+$); 143 (M—C$_6$H$_4$OCl)
Analysis: Calcd. for C$_{11}$H$_8$FN$_2$O$_3$Cl: C=48.81; H=2.98; N=10.35; F=7.02. Found: C=48.73; H=3.02; N=10.42; F=7.13.

EXAMPLE II

Proceeding as described in Example I using ethoxychloromethane (2.835 g, 30 m. mol) as the halide and performing the reaction at 30° C. for 1 hour, three products were obtained in the following order having the following physical characteristics:

$N^1,N^3$-di(ethoxymethyl)-5-fluorouracil: 1.354 g (36.7% yield), m.p. 55° C.
NMR(CDCl$_3$): δ ppm; 1.21 (6H, triplet), 3.60 (2H, quartet), 3.65 (2H, quartet), 5.16 (2H, singlet), 5.42 (2H, singlet), 7.47 (2H, doublet)
IR(KBr): ν cm$^{-1}$; 1730, 1670

UV(Dioxane-H$_2$O; 50%): λ$_{max}^{pH=7.0}$, nm(ε); 268 (7600)
Mass spectrum: m/e = 246 (M$^+$), 202 (M—C$_2$H$_4$O)
Analysis: Calcd. for C$_{10}$H$_{15}$FN$_2$O$_4$: C=48.78; H=6.14; N=11.38; F=7.72. Found: C=48.42; H=6.22; N=11.54; F=7.27.

N$^1$-ethoxymethyl-5-fluorouracil: 0.231 g (4.1% yield), m.p. 136° C.
NMR(CDCl$_3$): δ ppm; 1.20 (3H, triplet), 3.55 (4H, quartet), 5.05 (2H, singlet), 7.32 (1H, doublet)
IR(KBr): ν cm$^{-1}$; 1710, 1670
UV(Dioxane-H$_2$O; 50%): λ$_{max}^{pH=7.0}$, nm(ε), 266 (7600)
Mass specturm: m/e = 188 (M$^+$), 159 (M—C$_2$H$_4$), 144 (M—C$_2$H$_4$O)
Analysis: Calcd. for C$_7$H$_9$FN$_2$O$_3$: C=44.68; H=4.82; N=14.88; F=10.10. Found: C=44.70; H=4.92; N=14.78; F=9.99.

N$^3$-ethoxymethyl-5-fluorouracil: 0.225 g (4.0% yield), m.p. 118° C.
NMR(CDCl$_3$): δ ppm; 1.17 (3H, triplet), 3.00 (2H, quartet), 5.32 (2H, singlet), 7.30 (1H, doublet)
IR(KBr): ν cm$^{-1}$; 1720, 1670
UV(Dioxane-H$_2$O; 50%): λ$_{max}^{pH=7.0}$, nm(ε); 267
Mass spectrum: m/e = 188 (M$^+$), 144 (M—C$_2$H$_4$O)
Analysis: Calcd. for C$_7$H$_9$FN$_2$O$_3$: C=44.68; H=4.82; N=14.89; F=10.10. Found: C=44.81; H=4.80; N=14.91; F=10.14.

EXAMPLE III

Proceeding as described in Example I using methoxychloromethane as the halide, two products were obtained having the following physical characteristics:
N$^1$,N$^3$-di-(methoxymethyl)-5-fluorouracil
NMR(CDCl$_3$): δ ppm; 7.45 (1H, doublet), 4.91 (2H, singlet), 4.66 (2H, singlet), 2.97 (3H, singlet), 2.93 (3H, singlet)
IR(film): ν cm$^{-1}$; 1720, 1660
UV(Dioxane-H$_2$O; 50%): λ$_{max}^{pH=7.0}$, nm(ε); 268 (10400)
Mass spectrum: m/e = 218 (M$^+$), 203 (M—CH$_3$), 188 (M—CH$_3$O)
Analysis: Calcd. for C$_8$H$_{11}$FN$_2$O$_4$: C=44.04; H=5.08; N=12.84; F=8.71. Found: C=43.74; H=5.19; N=12.59; F=8.56.

N$^1$-methoxymethyl-5-fluorouracil: m.p. 134° C.
NMR(CDCl$_3$): δ ppm; 7.48 (1H, doublet), 5.09 (2H, singlet), 3.40 (3H, singlet)
IR(KBr): ν cm$^{-1}$; 1700, 1360, 1220, 1090
Mass spectrum: m/e = 174 (M$^+$), 100, 45

EXAMPLE IV

Proceeding as described in Example I using propoxychloromethane as the halide, two products were obtained having the following physical characteristics:
N$^1$,N$^3$-di-(propoxymethyl)-5-fluorouracil
NMR(CDCl$_3$): δ ppm; 7.42 (1H, doublet), 5.46 L (2H, singlet), 5.19 (2H, singlet), 3.7–3.4 (4H, multiplet), 1.85–1.4 (4H, multiplet), 1.05–0.8 (6H, multiplet)
IR(film): ν cm$^{-1}$; 1730, 1695, 1675
Mass spectrum: m/e = 274 (M$^+$), 43
N$^1$-propoxymethyl-5-fluorouracil: m.p. 66° C.
IR(KBr): ν cm$^{-1}$; 1735, 1720, 1700
NMR(CDCl$_3$): δ ppm; 9.27 (1H, singlet), 7.43 (1H, doublet), 5.17 (2H, singlet), 3.52 (2H, triplet), 1.8–1.4 (2H, multiplet), 0.93 (3H, triplet)
Mass spectrum: m/e = 202 (M$^+$), 73

Analysis: Calcd. for C$_8$H$_{11}$O$_3$N$_2$F: C=47.52; H=5.48; N=13.86. Found: C=47.24; H=5.61; N=13.58.

EXAMPLE V

Proceeding as described in Example I using butoxychloromethane as the halide, two products were obtained having the following physical characteristics:
N$^1$,N$^3$-di-(butoxymethyl)-5-fluorouracil
IR(film): δ cm$^{-1}$; 1730, 1690, 1670
NMR(CDCl$_3$): ν ppm; 7.42 (1H, doublet), 5.44 (2H, singlet), 5.19 (2H, singlet), 3.7–3.4 (4H, multiplet), 1.75–1.15 (8H, multiplet), 1.05–0.8 (6H, multiplet)
Mass spectrum: m/e = 302 (M$^+$), 57
N$^1$-butoxymethyl-5-fluorouracil: m.p. 70° C.
IR(KBr): δ cm$^{-1}$; 1700, 1100
NMR (CDCl$_3$): ν ppm; 9.6 (1H, singlet), 7.38 (1H, doublet) 5.12 (2H, singlet), 3.52 (2H, triplet) 1.1–1.75 (4H, multiplet), 0.90 (3H, triplet)
Mass spectrum: m/e = 216 (M$^+$), 142, 130, 57
UV(Dioxane-H$_2$O; 50%): λ$_{max}^{pH=7.0}$, nm (ε), 266 (8200)
Analysis: Calcd. for C$_9$H$_{13}$N$_2$FO$_3$: C=50.00; H=6.06; N=13.00. Found: C=49.77; H=6.27 N=12.84.

EXAMPLE VI

Proceeding as described in Example I using heptoxychloromethane as the halide, N$^1$-heptoxymethyl-5-fluorouracil was obtained having the following physical characteristics:
N$^1$-heptoxymethyl-5-fluorouracil: m.p. 81.5° C.
IR(KBr): ν cm$^{-1}$; 1730, 1695, 1100
NMR(CDCl$_3$): δ ppm; 9.4 (1H, singlet), 7.37 (1H, doublet), 5.12 (2H, singlet), 3.51 (2H, triplet), 1.50 (2H, multiplet), 1.26 (8H, multiplet), 0.86 (3H, triplet)
Mass spectrum: m/e 258 (M$^+$), 143, 129, 57
UV(Dioxane-H$_2$O; 50%): λ$_{max}^{pH=7.0}$, nm(ε), 266
Analysis: Calcd. for C$_{12}$H$_{19}$N$_2$FO$_3$: C=55.80; H=57.41; N=10.85. Found: C=55.58; H=7.66; N=10.74.

EXAMPLE VII

Proceeding as described in Example I using isopropoxychloromethane as the halide, two products were obtained having the following physical characteristics:
N$^1$,N$^3$-di-(isopropoxymethyl)-5-fluorouracil
IR(film): ν cm$^{-1}$; 1720, 1670, 1460
NMR(CDCl$_3$): δ ppm; 7.48 (1H, doublet), 5.46 (2H, singlet), 5.23 (2H, singlet), 3.88 (2H, heptet), 1.21 (6H, doublet)
Mass spectrum: m/e = 274 (M$^+$), 215, 73, 43
N$^1$-isopropoxymethyl-5-fluorouracil: m.p. 115° C.
IR(KBr): ν cm$^{-1}$, 1720, 1695, 1655
NMR(CDCl$_3$): δ ppm; 7.45 (1H, doublet), 5.17 (2H, singlet), 3.82 (1H, heptet), 1.22 (6H, doublet)
Mass spectrum: m/e = 202 (M$^+$), 172, 143, 130, 73
Analysis: Calcd. for C$_8$H$_{11}$N$_2$O$_3$F: C=47.52; H=5.48; N=13.89. Found: C=47.47; H=5.58; N=13.64.

EXAMPLE VIII

Proceeding as described in Example I using phenoxychloromethane as the halide, N$^1$-phenoxymethyl-5-fluorouracil was obtained having the following physical characteristics:
m.p. 150° C.

IR(KBr): ν cm$^{-1}$; 1690, 1660, 1600, 1230

NMR(CDCl$_3$-DMSO-d$_6$): δ ppm; 11.2 (1H, singlet), 7.47 (1H, doublet), 6.9–7.4 (5H, multiplet), 5.65 (2H, singlet)

Mass spectrum: m/e = 236 (M$^+$), 143, 100, 94

EXAMPLE IX

Proceeding as described in Example I using p-methoxyphenoxychloromethane as the halide, N$^1$-p-methoxyphenoxymethyl-5-fluorouracil was obtained having the following physical characteristics:

m.p. 110° C.

IR(KBr): ν cm$^{-1}$; 1730, 1710, 1675, 1505

NMR(CDCl$_3$-DMSO-d$_6$): δ ppm; 11.05 (1H, singlet), 7.43 (1H, doublet), 6.73–7.03 (4H, multiplet), 5.58 (2H, singlet), 3.77 (3H, singlet)

Mass spectrum: m/e = 266 (M$^+$), 124, 100

EXAMPLE X

Proceeding as described in Example I using 2,2,2-trifluoroethoxychloromethane as the halide, N$^1$-2,2,2-trifluoroethoxymethyl-5-fluorouracil was obtained having the following physical characteristics:

m.p. 114° C.

IR(KBr): ν cm$^{-1}$; 1735, 1675

NMR(Acetone-d$_6$): δ ppm; 7.92 (1H, doublet), 5.33 (2H, singlet) 4.24 (2H, quartet)

Mass spectrum: m/e = 242 (M$^+$), 113

Analysis: Calcd. for C$_7$H$_6$O$_3$N$_2$F$_4$: C=34.72; H=2.497; N=11.57. Found: C=34.75; H=2.43; N=11.62.

EXAMPLE XI

Proceeding as described in Example I using 2-fluoroethoxychloromethane as the halide, N$^1$-2-fluoroethoxymethyl-5-fluorouracil was obtained having the following physical characteristics:

m.p. 121° C.

NMR(CDCl$_3$): δ ppm; 7.39 (1H, doublet), 5.20 (2H, singlet), 4.79 (1H, multiplet), 4.32 (1H, multiplet), 4.01 (1H, multiplet), 3.72 (1H, multiplet)

Mass spectrum: m/e = 206 (M$^+$), 143, 100, 114

Analysis: Calcd. for C$_7$H$_8$O$_3$N$_2$F$_2$: C=40.78; H=3.91; N=13.59. Found: C=41.09; H=4.10; N=13.64.

EXAMPLE XII

Proceeding as described in Example I using 2,2,2,-trichloroethoxychloromethane as the halide, N$^1$-2,2,2-trichloroethoxymethyl-5-fluorouracil was obtained having the following physical characteristics:

m.p. 206° C.

IR(KBr): ν cm$^{-1}$; 3050, 2860, 1710, 1660

NMR(Acetone-d$_6$): δ ppm; 7.97 (1H, doublet), 5.47 (2H, singlet), 4.45 (2H, singlet)

Mass spectrum: m/e = 290 (M$^+$), 292, 294, 100

EXAMPLE XIII

Proceeding as described in Example I using 2-chloroethoxychloromethane as the halide, two products were obtained having the following physical characteristics:

N$^1$-2-chloroethoxymethyl-5-fluorouracil: m.p. 111° C.

IR(KRr): ν cm$^{-1}$; 3100, 2860, 1710, 1670

NMR(CDCl$_3$): δ ppm; 9.45 (1H, singlet), 7.42 (1H, doublet), 5.21 (2H, singlet), 3.97–3.57 (4H, multiplet)

Mass spectrum: m/e = 222 (M$^+$), 224, 100, 93, 63

N$^1$,N$^3$-di-(2-chloroethoxymethyl)-5-fluorouracil

IR(film): δ cm$^{-1}$; 1725, 1670, 1460

NMR(CDCl$_3$): δ ppm; 7.49 (1H, doublet), 5.475 (2H, doublet), 5.24 (2H, singlet), 4.02–3.54 (8H, multiplet)

Mass spectrum: m/e = 314 (M$^+$), 93, 114, 223, 235, 63

EXAMPLE XIV

Proceeding as described in Example I using cyclobutoxychloromethane as the halide, N$^1$-cyclobutoxymethyl-5-fluorouracil was obtained having the following physical characteristics:

N$^1$-cyclobutoxymethyl-5-fluorouracil: m.p. 119° C.

NMR(CDCl$_3$): δ ppm; 9.95 (1H, singlet), 7.43 (1H, doublet), 5.10 (2H, singlet), 4.105 (1H, quintet), 2.4–1.3 (6H, multiplet)

Mass spectrum: m/e = 214 (M$^+$), 186, 143, 100

Analysis: Calcd. for C$_9$H$_{11}$O$_3$N$_2$F: C=50.47; H=5.18; N=13.08. Found: C=50.83; H=5.46; N=12.93.

EXAMPLE XV

Proceeding as described in Example I using cyclopentoxychloromethane as the halide, N$^1$-cyclopentoxymethyl-5-fluorouracil was obtained having the following physical characteristics:

N$^1$-cyclopentoxymethyl-5-fluorouracil: m.p. 125° C.

NMR(CDCl$_3$): δ ppm; 9.95 (1H, singlet), 7.43 (1H, doublet), 5.14 (2H, singlet), 4.10(1H, multiplet), 1.9–1.4 (8H, multiplet)

Analysis: Calcd. for C$_{10}$H$_{13}$O$_3$N$_2$F: C=52.63; H=5.74; N=12.27. Found: C=52.70; H=5.91; N=12.16.

EXAMPLE XVI

Proceeding as described in Example I using cyclohexoxychloromethane as the halide, N$^1$-cyclohexoxymethyl-5-fluorouracil was obtained having the following physical characteristics:

N$^1$-cyclohexoxymethyl-5-fluorouracil: m.p. 158° C.

NMR(Acetone-d$_6$): δ ppm; 10.4 (1H, singlet), 7.83 (1H, singlet), 7.83 (1H, doublet), 5.19 (2H, singlet), 3.58 (1H, multiplet), 2.2–1.7 (10H, multiplet)

Mass spectrum: m/e = 242 (M$^+$), 131, 212, 83

Analysis: Calcd. for C$_{11}$H$_{15}$O$_3$N$_2$F: C=54.54; H=6.24; N=11.56. Found: C=54.67; H=6.45; N=11.42.

EXAMPLE XVII

Proceeding as described in Example I using allyloxychloromethane as the halide, N$^1$-allyloxymethyl-5-fluorouracil was obtained having the following physical characteristics:

N$^1$-allyloxymethyl-5-fluorouracil: m.p. 79° C.

IR(KBr): ν cm$^{-1}$; 2850, 1690, 1660, 1450

NMR(CDCl$_3$): δ ppm; 10.08 (1H, singlet), 7.44 (1H, doublet), 6.1–5.7 (1H, multiplet), 5.44–5.7 (1H, multiplet, 5.44–5.15 (2H, multiplet), 5.18 (2H, singlet), 4.105 (2H, triplet-doublet)

Mass spectrum: m/e = 200 (M$^+$), 143, 100, 70, 41

Analysis: Calcd. for C$_8$H$_9$O$_3$N$_2$F: C=48.00; H=4.53; N=13.995. Found: C=47.94; H=4.68; N=13.90.

EXAMPLE XVIII

Proceeding as described in Example I using methoxyethoxychloromethane as the halide, N$^1$-methoxyethoxymethyl-5-fluorouracil was obtained having the following physical characteristics:

$N^1$-methoxyethoxymethyl-5-fluorouracil: m.p. 113° C.

IR(KBr): δ cm$^{-1}$; 2830, 1720, 1700, 1670

NMR(CDCl$_3$-DMSO-d$_6$): δ ppm; 7.59 (1H, doublet), 5.16 (2H, singlet), 3.46–3.8 (4H, multiplet), 3.34 (3H, singlet)

Mass spectrum: m/e = 218 (M$^+$), 143, 100, 89, 59

Analysis: Calcd. for C$_8$H$_{11}$N$_2$O$_4$F: C=44.04; H=5.08; N=12.84. Found: C=44.16; H=5.36; N=12.72.

EXAMPLE XIX

Proceeding as described in Example I using ethoxyethoxychloromethane as the halide, $N^1$-ethoxyethoxymethyl-5-fluorouracil was obtained having the following physical characteristics:

$N^1$-ethoxyethoxymethyl-5-fluorouracil: m.p. 85°°C.

IR(KBr): ν cm$^{-1}$; 1710, 1680, 1470, 1350

NMR(CDCl$_3$): δ ppm; 9.76 (1H, singlet), 7.46 (1H, doublet), 5.19 (2H, singlet), 3.84–3.40 (6H, multiplet), 1.19 (3H, triplet)

Mass spectrum: m/e = 232 (M$^+$), 143, 103

Analysis: Calcd for C$_9$H$_{13}$O$_4$N$_2$F: C=46.55; H=5.64; N=12.07. Found: C=46.55; H=5.95; N=11.96.

EXAMPLE XX

Proceeding as described in Example I using phenoxyethoxychloromethane as the halide, $N^1$-phenoxyethoxymethyl-5-fluorouracil was obtained having the following physical characteristics:

$N^1$-phenoxyethoxymethyl-5-fluorouracil: m.p. 122° C.

IR(KBr): δ cm$^{-1}$; 3030, 1690, 1600, 1490, 1460

NMR(CDCl$_3$): δ ppm; 9.25 (1H, singlet), 7.41 (1H, doublet), 7.4–6.8 (5H, multiplet), 5.23 (2H, singlet), 4.2–3.89 (4H, multiplet)

Mass spectrum: m/e = 280 (M$^+$), 187, 121, 77

EXAMPLE XXI

Proceeding as described in Example I using acetoxyethoxychloromethane as the halide, $N^1$-acetoxyethoxymethyl-5-fluorouracil was obtained having the following physical characteristics:

m.p. 145° C.

NMR(CDCl$_3$): δ ppm; 8.86 (1H, singlet), 7.39 (1H, doublet), 5.18 (2H, singlet), 4.32–4.15 (2H, multiplet), 3.88–3.70 (2H, multiplet), 2.09 (3H, singlet)

Mass spectrum: m/e = 246 (M$^+$), 143, 117, 100, 130, 87

Analysis: Calcd. for C$_9$H$_{11}$O$_5$N$_2$F: C=43.91; H=4.50; N=11.38. Found: C=43.74; H=4.65; N=11.12.

EXAMPLE XXII $N^1$-acetoxyethoxymethyl-5-fluorouracil was reacted with 1N NaOH for 1 hour at 40° C. to obtain $N^1$-2-hydroxyethoxymethyl-5-fluorouracil.

$N^1$-2-hydroxyethoxymethyl-5-fluorouracil: m.p. 154° C.

NMR(Pyridine-d$_6$): δ ppm; 8.04 (1H, doublet), 5.40 (2H, singlet), 4.1–3.8 (4H, multiplet)

Mass spectrum: m/e = 204 (M$^+$), 174, 159, 143, 130, 131

Analysis: Calcd. for C$_7$H$_9$O$_4$N$_2$F: C=41.18; H=4.44; N=13.72. Found: C=41.34; H=4.72; N=13.61.

What is claimed is:
1. $N^1$-(p-chlorophenoxymethyl)-5-fluorouracil.
2. $N^1$-ethoxymethyl-5-fluorouracil.
3. $N^3$-ethoxymethyl-5-fluorouracil.
4. $N^1$-propoxymethyl-5-fluorouracil.
5. $N^1$-isopropoxymethyl-5-fluorouracil.
6. $N^1$-phenoxyethoxymethyl-5-fluorouracil.
7. $N^1$-2-chloroethoxymethyl-5-fluorouracil.
8. $N^1$-cyclopentoxymethyl-5-fluorouracil.

* * * * *